US006762410B1

(12) United States Patent
Wiechers et al.

(10) Patent No.: US 6,762,410 B1
(45) Date of Patent: Jul. 13, 2004

(54) ANALYSIS APPARATUS

(75) Inventors: Joachim Wiechers, Planegg (DE); Rainer Riesenberg, Jena (DE); Eckard Kopatzki, Hoehenkirchen-Siegertsbrunn (DE)

(73) Assignee: CS Clean Systems AG, Ismaning (DE)

( * ) Notice: Subject to any disclaimer, the term of this patent is extended or adjusted under 35 U.S.C. 154(b) by 80 days.

(21) Appl. No.: 09/937,547

(22) PCT Filed: Jun. 7, 2000

(86) PCT No.: PCT/EP00/05262
§ 371 (c)(1),
(2), (4) Date: Sep. 26, 2001

(87) PCT Pub. No.: WO00/75640
PCT Pub. Date: Dec. 14, 2000

(30) Foreign Application Priority Data

Jun. 8, 1999 (DE) .......................... 199 26 121

(51) Int. Cl.⁷ .............................................. G01N 21/35
(52) U.S. Cl. ........................................ 250/343; 250/345
(58) Field of Search ................................ 250/343, 345, 250/346

(56) References Cited

U.S. PATENT DOCUMENTS

| 3,734,631 A | | 5/1973 | Justice et al. | |
|---|---|---|---|---|
| 3,916,195 A | * | 10/1975 | Burch et al. | ................. 250/345 |
| 4,281,248 A | | 7/1981 | Fabinski | |
| 4,950,900 A | | 8/1990 | Takeuchi et al. | |
| 5,550,375 A | * | 8/1996 | Peters et al. | ................. 250/343 |
| 5,689,114 A | * | 11/1997 | Miyazaki et al. | ........... 250/343 |
| 5,693,944 A | | 12/1997 | Rich | |
| 5,764,354 A | | 6/1998 | Aidam et al. | |
| 5,874,737 A | | 2/1999 | Bytyn et al. | |
| 5,876,674 A | | 3/1999 | Dosoretz | |
| 6,075,246 A | | 6/2000 | Stock | |
| 6,191,421 B1 | | 2/2001 | Yamamori et al. | |

FOREIGN PATENT DOCUMENTS

| DE | G 94 20 231.1 U1 | 3/1985 |
|---|---|---|
| DE | 34 37 397 A1 | 4/1986 |
| DE | 40 02 436 A1 | 8/1991 |
| DE | 44 37 188 A | 4/1996 |
| DE | 198 08 128 A | 8/1998 |
| DE | 197 42 053 C1 | 1/1999 |
| EP | 0 780 681 A2 | 6/1997 |
| EP | 0 794 423 A1 | 9/1997 |
| EP | 0 834 732 A2 | 4/1998 |
| EP | 0 332 180 A2 | 9/1999 |

* cited by examiner

Primary Examiner—Constantine Hannaher
(74) Attorney, Agent, or Firm—Flynn, Thiel, Boutell & Tanis, P.C.

(57) ABSTRACT

An apparatus for measuring the concentration of a substance in a specimen. The apparatus includes a housing that defines a chamber for the specimen. A radiation source mounted to the housing emits radiation at a wavelength at which the radiation is absorbed by the substance. Two spaced apart receivers are mounted to the housing. Both receivers detect radiation at the wavelength at which it is absorbed by the specimen. Two concave mirrors are disposed in the housing. The mirrors are positioned to split the radiation emitted by the source into two beams, each of the beams being directed to a separate one of the receivers and so that the paths of travel of the beams from the source to the separate receivers are of different lengths. The concentration of the substance is determined by based on the difference in radiation detected by the receivers.

23 Claims, 3 Drawing Sheets

ANALYSIS APPARATUS

FIELD OF THE INVENTION

This invention relates to an analyzer for determining the concentration of one or more substances in a mixture by measuring the concentration-dependent molecule-specific extinction.

BACKGROUND OF THE INVENTION

Nondispersive photometers for determining the concentration of a substance in a mixture are widely known and used for a great variety of measuring tasks. Thus, commercial medical measuring instruments for determining $CO_2$ content in tidal air, so-called capnometers, are based on this principle. These devices evaluate the attenuation of introduced infrared radiation at the wavelength of 4.26 micrometers characteristic of $CO_2$ according to Lambert-Beer's law $$I = I_0 \exp[-kCL]$$

where
- I: Detected intensity
- $I_0$: Irradiated intensity
- k: Specific extinction coefficient
- C: Concentration
- L: Optical path length as a measure of the $CO_2$ concentration present in the sample.

In the simplest form, nondispersive photometers work according to a single-beam method (See EP 0 794 423 A1).

IR radiation having an intensity assumed to be constant is passed from a radiation source through the volume penetrated by the sample under testing and measured therebehind for its intensity. The measurement is performed using an optoelectric detector as a radiation receiver. The selectivity for the substance to be detected is ensured by restricting the IR spectrum to the characteristic wavelengths) by a narrow-band filter disposed either behind the radiator or in front of the receiver.

Alternatively, unfiltered light is passed behind the absorption chamber in a closed chamber filled with the substance to be determined, in which chamber the radiant energy of the radiation source attenuated at the characteristic wavelength (s) in accordance with the concentration present in the absorption chamber is converted into thermal energy by optical excitation at exactly the characteristic wavelength(s) and detected as pressure (optopneumatic detector).

In order to obtain the signal-to-noise ratio required for the necessary measuring accuracy, periodic modulation of the signal is imperative. This is classically effected by the use of rotating beam chopping disks, so-called choppers. Since these are mechanically moving parts, this solution has inherent disadvantages with respect to minimum attainable size, interference susceptibility due to the action of external force, and perturbing effects such as vibrations or sound caused by the rotation. In modern devices one therefore uses compact, thermal thin-film or thick-film radiation sources which are operated with clocked current and thus emit periodically modulated radiation themselves.

The single-beam method with one radiation source and one receiver is seldom employed. This is because temperature and intensity fluctuations and aging phenomena of the radiation source, optical elements and receiver lead to strong drift of the output signal. In order to compensate for these effects, one usually employs a double-beam method which uses a second radiation path not influenced by the substance to be measured as a reference. The signals of the first (measuring) and second (reference) radiation paths are ratioed. The ratio is used for determining the concentration.

Double-beam methods by which the radiation from the radiation source is split into measuring and reference radiation paths to two receivers can be realized with optical devices differing in the number of radiation sources, cells and/or receivers. A device with two radiation sources, one cell and two receivers is described in U.S. Pat. No. 3,734,631. Compensation of thermal and aging effects in the cell is intrinsic to the method. Moreover, considerable measuring and automatic-control effort is necessary for keeping the radiant power of the two radiation sources constant, for instance by using two additional receivers for measuring the radiant power emitted by the radiation sources before the cell is traversed. A simplification of this assembly in that both radiation paths are passed onto one receiver is described in U.S. Pat. No. 4,899,053. However, no stabilization of the intensities of the two radiation sources is provided.

Intensity fluctuations due to temperature fluctuations or signs of aging of the radiation source can be compensated intrinsically if both radiation paths, i.e. the reference and measuring radiation paths, are operated from the same radiation source. For this purpose one must perform beam splitting which is typically realized by prisms or semitransparent, partially dichroic mirrors in front of or behind the absorption chamber (See EP 0 834 732 A2).

However, such optical components reduce intensity, which reduces the signal-to-noise ratio and thus worsens the lower detection limit. Furthermore, the spectral properties of such elements can change in the course of time through deposits or attack by aggressive media, which can lead to a shift of the intensity ratio between measuring and reference paths.

Advantageous beam splitting via imaging mirrors within the sample chamber doing without intensity-attenuating elements is described in DE 44 37 188 C2. The central requirement for the reference path is that its intensity not be influenced, or influenced substantially less than the measuring path, by concentration changes in the substance to be measured. For this purpose the reference path is guided almost completely through a transparent block of calcium fluoride in the interior of which there is no attenuation of light by the substance to be measured. However, such a block can cloud in the course of time through attack by aggressive media. More-over, exact adjustment of the mirrors and thus an elaborate adjusting device is necessary. Also, the adjustable mirrors form gaps and similar cavities which delay the exchange of the substance to be measured and thus lead to memory effects.

According to EP 0 780 681 A2, the reference beam traverses a reference cell filled with reference gas, but this involves the above-described disadvantages of prismatic beam splitting. Furthermore, it does not permit changes in the optical properties of the measuring cell to be detected. The miniaturization of such assemblies is limited.

Alternatively, measuring and reference beams are both guided through the measuring cell but measured in different wave ranges. The reference beam is either measured in such broadband fashion that the intensity change through extinction at the characteristic wavelengths of the substance to be measured is irrelevant, or it is measured in narrow-fashion band like the measuring beam but at another wavelength. The disadvantage of the first method is that a change in spectral distribution of the radiation source due to temperature fluctuations or signs of aging will generally influence measuring and reference signals differently. The disadvantage of the second method is the uncertainty about the nonoccurrence of absorption at the reference wavelength due to unknown substances. This is dangerous specifically in the case of ambient air monitoring for toxic gases since absorption at the reference wavelength leads to a reduction of sensitivity in the measuring path.

According to U.S. Pat. No. 4,281,248 the radiation of an IR radiation source is supplied to optopneumatic detectors with a chopper alternatively via a reference radiation path and a measuring radiation path. The gas to be measured flows through a long cell in the measuring radiation path and then through a short cell in the reference radiation path.

According to U.S. Pat. No. 5,876,674 the radiation of a radiation source is split into two radiation paths and the gas to be measured guided through an absorption chamber having in each radiation path two optical elements formed as aligned glass rods each at different distance so that the optical path length in the absorption chamber is greater between one pair of optical elements than with the other pair.

SUMMARY OF THE INVENTION

The object of the invention is to provide an analyzer for determining concentration by transmission measurement which is compact and stable toward outside mechanical and thermal influences and permits a wide concentration range—from a few ppm to several ten percent—to be determined reliably and continuously.

According to the invention, two radiation paths, i.e. a first radiation path from the radiation source to a first receiver and a second radiation path from the radiation source to a second receiver, traverse the absorption chamber containing the sample with the substance the concentration of which is to be determined.

In both radiation paths measuring is performed at the same wavelength. However, the two radiation paths have different lengths, the fist being substantially longer than the second, preferably at least twice, in particular at least four times, as long. This causes the radiation passing along the first, long path to be attenuated more in the presence of the substance to be detected than the radiation along the second, shorter path.

In delimitation over the prior art, the two radiation paths are thus not only guided completely through the sample to be measured but are furthermore measured at the same wavelength. This results in optical equivalence of the two beams which avoids essential disadvantages of the approaches hitherto described. Due to the equivalent beam control, any intensity-attenuating perturbing effects possibly occurring in the course of time act on both radiation paths to the same extent. Due to the measurement of both radiation paths at the same wavelength, the measuring result is independent of the spectral distribution of the radiation source, the spectral properties of the optical elements or changes thereof through aging effects since both radiation paths are influenced to the same extent by these factors.

The greatly different absorption paths in the two radiation paths furthermore permit the dynamic range of the device to be advantageously widened. If, at high concentrations of the substance to be measured, the absorption in the long radiation path is so strong that the signal arriving at the detector falls below the noise limit, the signal from the shorter radiation path can be evaluated directly. The attainable dynamic gain corresponds to the ratio of the two absorption paths.

From the radiation intensity measured by each receiver, one forms an intensity comparative value, for example the quotient of the intensities measured by the first and second receivers. This measured intensity comparative value or intensity quotient corresponds to a certain concentration of the substance to be measured. If one applies Lambert-Beer's law as mentioned above to both radiation paths, forms the quotient of the two equations, takes the logarithm and solves for concentration, one obtains $$C = -1/(kL_1 - kL_2) \ln(I_1/I_2)$$

On the other than, one can first logarithmize the two equations, expand them accordingly, subtract from each other and solve for irradiated intensity. One obtains $$I_0 = \exp[L_1 \ln I_2 - L_2 \ln I_1/(L_1 - L_2)]$$

Evaluation of the signals of both receivers thus permits not only the determination of concentration C but also a statement about irradiated power $I_0$. Even if this value is for technical reasons not used for controlling the radiation source, it can be used for redundant functional testing of the analyzer.

The method can be performed not only in a single-channel fashion, i.e. for determining the concentration of a substance in a sample, but also in multi-channel fashion, i.e. for simultaneously determining the concentrations of a plurality of substances in a mixture. In the latter case one requires a pair of radiation paths, a first long one and a second short one, for each individual channel to be measured. However, the radiation paths of all channels are operated from the same radiation source and guided through the same sample according to the invention.

The inventive analyzer or photometer is applicable in particular for determining substances in gas mixtures. However, it can also be used to determine the concentration of a substance in a liquid.

Due to the monolithic assembly and the resulting high mechanical stability, the inventive analyzer is compression-proof and also helium-leakproof. It can accordingly be used for measurements in the pressure range from vacuum to $10^6$ Pascals for example.

As radiation one uses in particular infrared radiation. The infrared radiation source irradiates the sample to be analyzed and the receivers or detectors measure the attenuation of the IR radiation. The selectivity for a certain substance is obtained by narrow-band filtering of the light to arrange in which the substance absorbs IR radiation as greatly as possible in a characteristic wave range through molecule vibrations.

As an IR radiation source one preferably uses a thermal IR radiation source; one also preferably uses thermal receivers, e.g. pyrodetectors or thermopiles. However, it is also possible to use alternative electrooptical radiation sources such as diode lasers which work at low temperatures, or gas lasers. As receivers one can also use quantum detectors.

To form the two optical paths of different lengths belonging to a channel in the absorption chamber one preferably provides two mirrors in the absorption chamber which are disposed at different distances from the IR radiation source and reflect radiation of the radiation source onto first and second receivers.

The mirrors are preferably formed according to the invention by concave mirrors, whereby one preferably uses aspheric mirrors, in particular mirrors whose surface is formed by a section of a spheroid. Thus the light emitted by the radiation source is focused almost completely onto the receivers.

As a radiation source one therefore uses according to the invention an IR plane radiator produced by the thin- or thick-film technique. Since plane radiators have an angular distribution of emission following the law of cosines and thus emit a strongly forward directed radiation in contrast to point or line radiators, their radiation can be focused especially advantageously onto the receivers. In order to be protected from aging through gas contact or destruction upon measurement of reactive gases, the radiation source is preferably disposed outside the absorption chamber, i.e., separated gastight by an optical window from the absorption chamber and thus the substance to be measured.

The filter for filtering out the wave range of IR radiation characteristic of the substance to be measured can be disposed on the radiation source or both receivers in the case of single-channel measurement. In the case of multi-channel measurement the filters must be mounted in front of the receivers.

If the filters are mounted in front of the receivers, they must have pairwise exactly identical optical properties. In order to avoid differences in optical properties, as occur for production reasons both between different batches of filter material and due to inhomogeneities on one and the same disk of a filter, the filters belonging to a channel are especially advantageously cut out of adjacent areas of one and the same filter disk.

The inventive analyzer preferably has a monolithic assembly. That is, the mirrors are formed integrally with the housing whose interior forms the absorption chamber. For integral formation with the housing, the mirrors can be produced by machining the inside of the housing, forming the mirrors when casting the housing or the like. One can thus also do without installation of the mirrors and adjustment of the mirrors.

So that the interior of the housing is accessible, the housing is preferably partite. The mirrors are then preferably formed integrally with the same housing part. Due to this monolithic assembly one also requires few seals.

Since the interior of the housing at the same time forms the absorption chamber there are no separating surfaces, dead volumes or mountings between housing and mirrors, absorption chamber and housing, etc., with the monolithic design of the inventive analyzer. One thus obtains not only fast media exchange without memory effects but also reliably maintains the imaging geometry of the inventive device in case of temperature changes or mechanical influences.

The integral formation of the mirrors with the housing or the one housing part on which they are provided results in first-order compensation of thermal expansions upon temperature changes which would lead to a change of the lengths of the two optical paths belonging to a channel relative to each other. At the same time, the integral formation of the mirrors with the housing or the one housing part obtains high mechanical stability and thus effectively prevents a signal change due to outside mechanical influences.

The housing is preferably made of metal. This ensures not only high stiffness and thus high mechanical stability but also fast temperature compensation, in particular through metals high thermal conductivity and low heat capacity in order to ensure a fast temperature balance.

Suitable metals have proved to be in particular aluminum materials, i.e. aluminum metal or aluminum alloys, in particular temper annealed metal or aluminum materials, in order to prevent slow drift through internal stresses and thereby ensure high long-term stability.

Apart from that, aluminum materials permit the mirrors to be easily worked out for example by machining. Moreover, mirror surfaces of aluminum materials have high IR reflectivity. Mirror surfaces of aluminum materials are also inert to most media or they form a corrosion-inhibiting protective layer, for example toward oxygen (air) or fluorine-containing compounds through $Al_2O_3$ or $AlF_3$ protective layer. This layer is generally so thin that the optical properties are not influenced.

A metal housing moreover ensures an electric and magnetic shielding, which is important in particular for very small signals. The electronic housing receiving the devices for signal processing can be fastened to the photometer housing with the absorption chamber, the radiation source, the two receivers and the two mirrors, thereby ensuring good shielding for the total signal path. The electronic housing is for this purpose preferably made of the same material as the photometer housing, also in order to prevent temperature stresses due to different temperature expansion coefficients.

The radiation of the radiation source is preferably modulated in order to be independent of background radiation on the receiver side. If one wants to do without mechanically moving parts (choppers), the radiation source must be designed so as to be electrically modulated.

The inventive analyzer can be used for example for analyzing environmentally harmful or toxic gas, in particular for continuous monitoring of waste gases, for example for monitoring waste-gas cleaning installations. Environmentally harmful gases which can be analyzed with the inventive device are in particular inert, fluorine-containing gases, for example fluorinated or perfluorinated hydrocarbons, nitrogen trifluoride or sulfur hexafluoride.

With the inventive device one can reliably and continuously determine the concentration of one or more substances of e.g. less than 1 ppm to 50% and more.

BRIEF DESCRIPTION OF THE DRAWINGS

In the following description, a single-channel embodiment and a double-channel embodiment of the inventive analyzer will be explained in more detail by way of example with reference to the drawings, in which.

DETAILED DESCRIPTION

Figure 1:
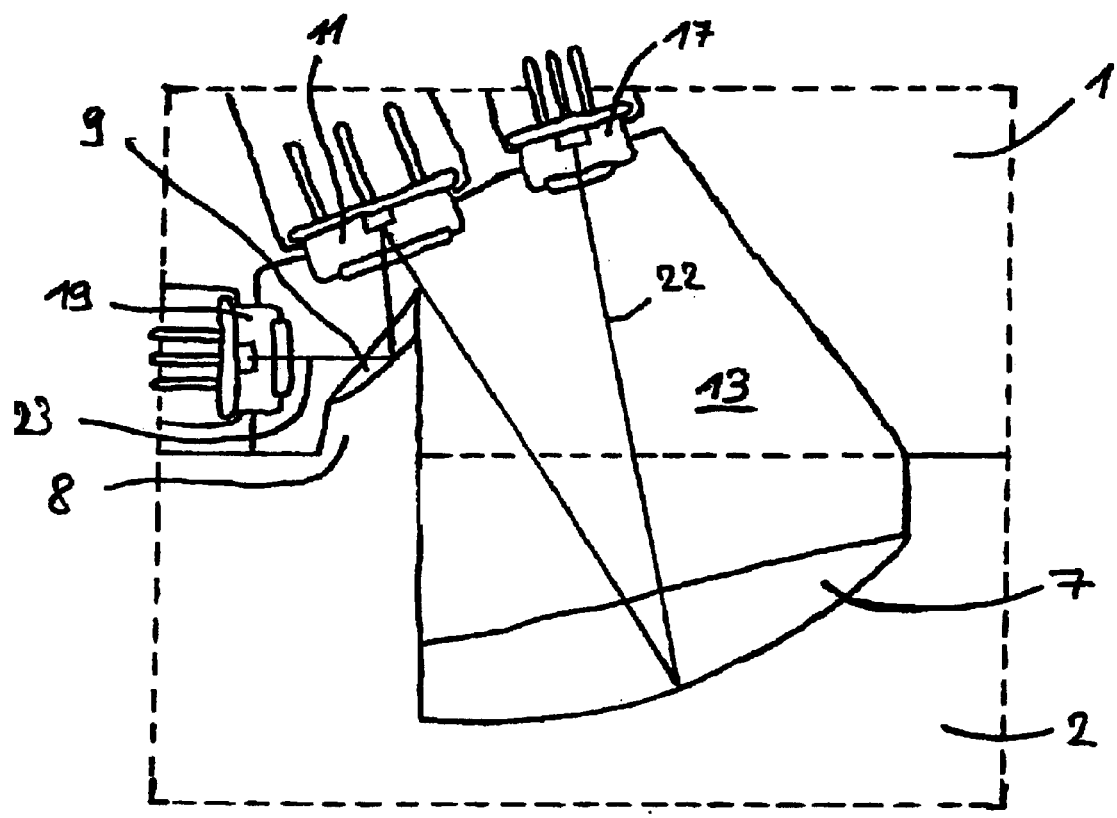
FIG. 1 shows schematically a view of the radiation path of the device.

The device accordingly has two housing parts 1, 2 of substantially equal size indicated by dashed lines in FIG. 1.

According to FIG. 2, housing half-members 1, 2 are of substantially cuboid form, for example made of an aluminum material. Between housing half-members 1, 2 there is sealing ring 3. Bores 4, 5 are for screwing housing half-members 1, 2 together.

A cavity is worked out of inside 6 of housing half-member 2 to form concave mirror 7. A projection 8 is worked out of inside 6 of housing half-member 2, and smaller second concave mirror 9 at the tip of projection 8. First concave mirror 7 is disposed at a substantially greater distance from IR radiation source 11 than second concave mirror 9. Concave mirrors 7, 9 integral with housing part 2 each form sections of a spheroid. The diameter of the spheroid of first concave mirror 7 being accordingly greater than the diameter of the spheroid of second concave mirror 9. Mirrors 7 and 9 are positioned so that the radiation source and one of the receivers are located at the focal points in each case. Inside 12 of housing part 1 likewise has a cavity for receiving projection 8, among other things.

The cavities on insides 6, 12 of housing parts 2, 1 form absorption chamber 13 of the mounted housing (FIG. 1).

Figure 2A:
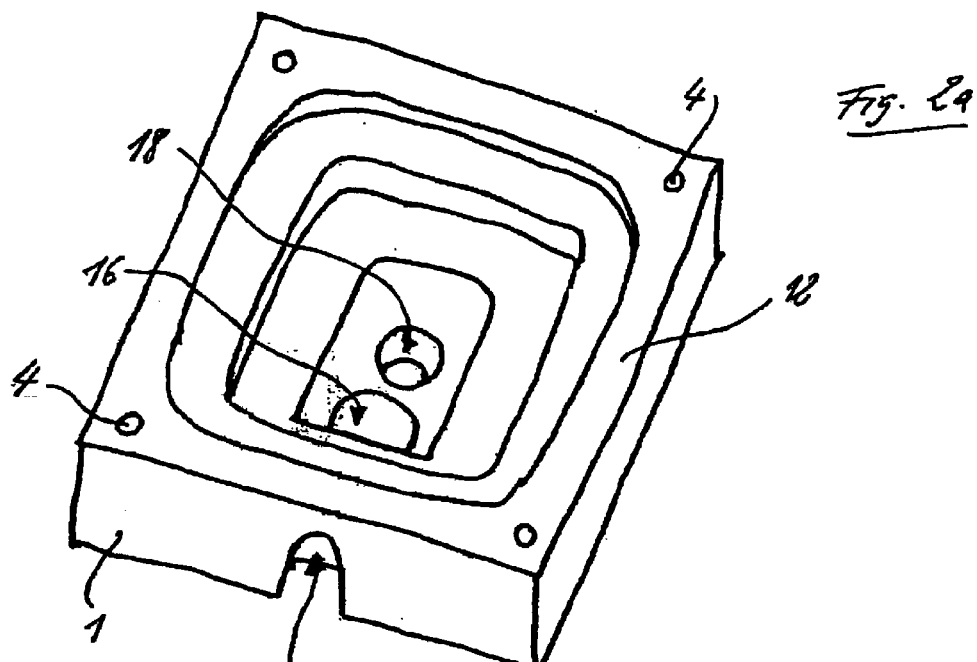
FIGS. 2a and 2b show perspective views of the two housing half-members of the double-channel device in the open state.
Figure 2B:
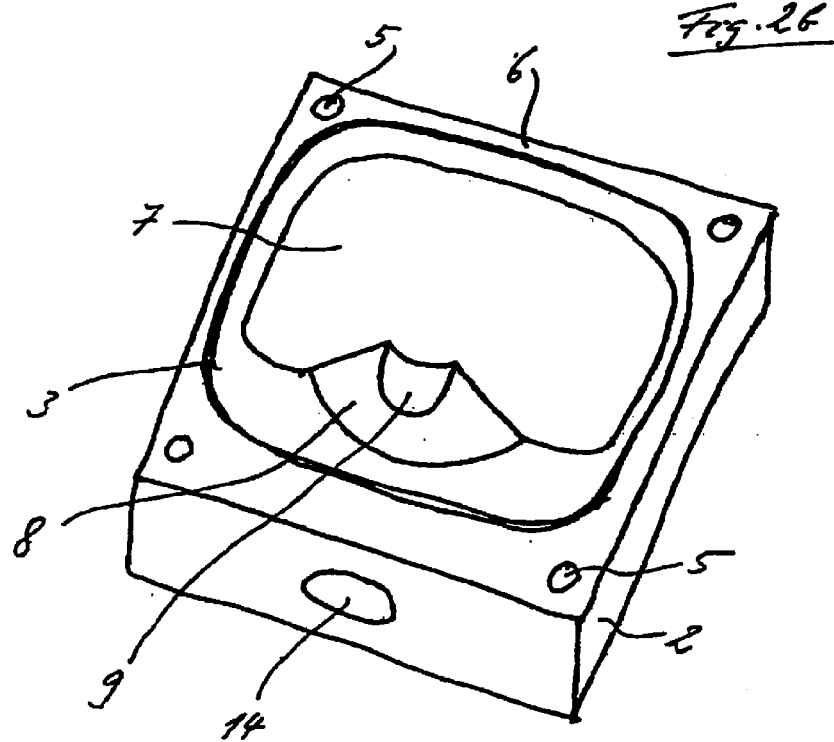

The medium to be analyzed is supplied to absorption chamber 13 via bore 14 in the wall of housing part 2 which is opposite mirror 7 (FIG. 2b). The medium exits through another bore (not shown) in housing part 1 or 2.

IR radiation source 11, formed as a plane radiator, is disposed outside housing part 1 and seats in an opening 16. Further, first receiver 17 is seated in opening 18 and second receiver 19 is seated in opening 21 in housing part 1 (FIG. 2).

According to FIG. 1, radiation from radiation source 11 is split on the edge of mirror 9 facing mirror 7 into radiation paths 22 and 23, preferably and especially advantageously in equal shares. Radiation paths 22, 23 from radiation source 11 to receivers 11, 19 traverse absorption chamber 13 and thus the substance to be analyzed contained therein. The one radiation path 22 by which part of the radiation from the radiation source is reflected by large mirror 7 has a substantially greater length than radiation path 22 with reflection on other mirror 9.

Figure 3A:
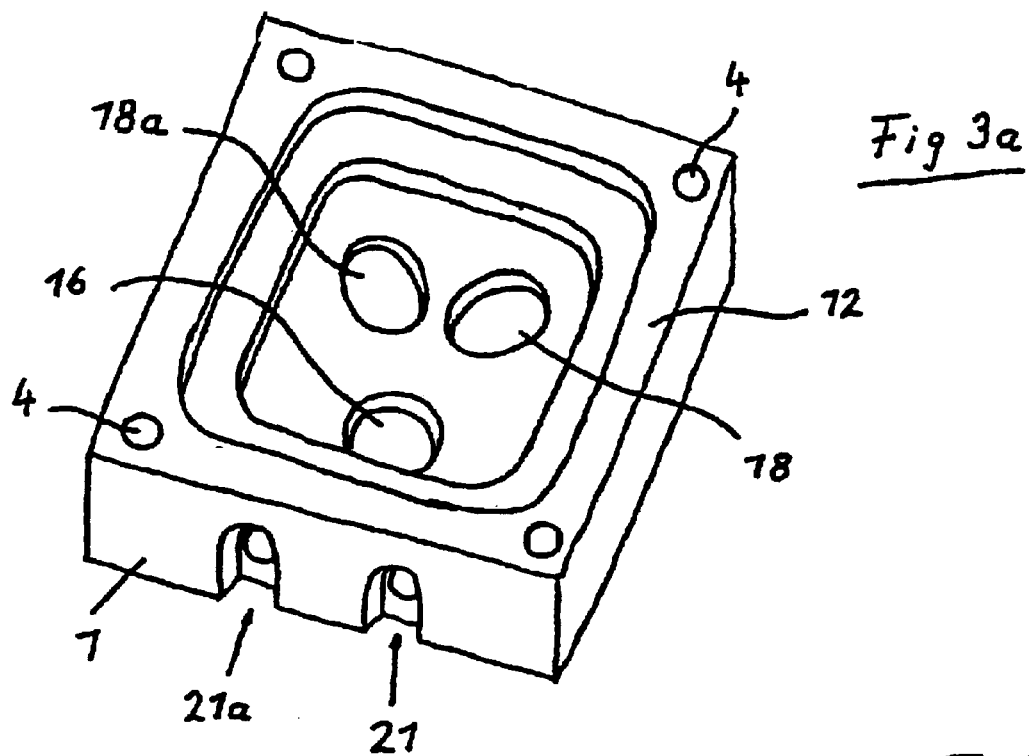
FIGS. 3a and 3b show perspective views of the two housing half-members of the double-channel device in the open state.
Figure 3B:
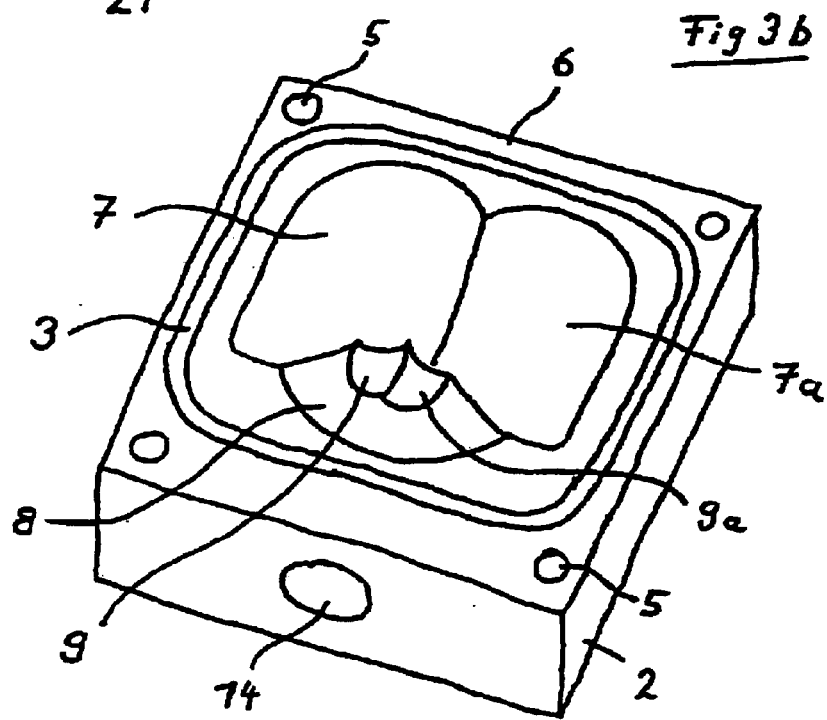

The double-channel configuration shown in FIGS. 3a and 3b differs from the single-channel configuration shown in FIGS. 2a and 2b only in the number of receivers and the formation of the mirrors. Instead of the single receivers in housing openings 18 and 21 in the single-channel configuration, one inserts two receivers in each case into housing openings 18 and 21, 18a and 21a (FIG. 3a) here. In the double-channel configuration, mirrors 7 and 9 of the single-channel configuration are broken in the plane shown in FIG. 1 and tilted away orthogonally therefrom such that the radiation source in housing opening 16 and the receivers in openings 18 and 21, 18a and 21a are seated at the focal points of mirrors and 9, 7a and 9a in each case (FIG. 3b).

What is claimed is:

1. An analysis apparatus, said apparatus including:
   a housing, said housing shaped to define an enclosed chamber for receiving a specimen to be analyzed;
   a radiation source mounted to said housing, said radiation source configured to emit radiation at a first wavelength that is absorbed by a first substance in the specimen, said radiation source being mounted to said housing to emit radiation into the chamber;
   a first pair of spaced-apart receivers mounted to said housing, each said receiver configured to measure radiation at the first wavelength and being mounted to said housing to receive radiation from within the chamber; and
   a first pair of concave mirrors that are disposed in the housing chamber, said mirrors being shaped and positioned in the chamber to split the radiation emitted by said source into two separate beams of the radiation, each beam of radiation being directed to a separate one of said receivers that form said first pair of said receivers and so that the paths of travel of the radiation beams from said source to said receivers are of different lengths.

2. The analysis apparatus of claim 1, wherein at least one of the two concave mirrors associated with the pair of receivers is formed as an aspheric concave mirror.

3. The analysis apparatus of claim 2, wherein the aspheric concave mirror constitutes a section of a spheroid.

4. The analysis apparatus of claim 1, wherein said radiation source is an electrically modulable plane radiator.

5. The analysis apparatus of claim 1, wherein said pair of concave mirrors are formed integrally with said housing so that said concave mirrors function as interior surfaces of said housing that define said chamber.

6. The analysis apparatus of claim 1, wherein:
   said housing is formed from a plurality of separate parts; and
   said first pair of concave mirrors are formed in one of said parts of said housing so that each said mirror functions as an interior surface of said housing that defines the chamber.

7. The analysis apparatus of claim 1, wherein:
   said housing is formed from a plurality of separate parts;
   said first pair of concave mirrors are formed in a first one of said parts of said housing so that each said mirror functions as an interior surface of said housing that defines the chamber; and
   said radiation source and said pair of receivers are mounted to a second one of said parts of said housing, the second part being separate from the first part.

8. The analysis apparatus of claim 7, wherein at least the first part of said housing is made of metal.

9. The analysis apparatus of claim 7, wherein the first part of said housing is made from aluminum.

10. The analysis apparatus of claim 1, wherein:
    said radiation source is further configured to emit radiation at a second wavelength that is different from the first wavelength, the second wavelength radiation being radiation that is absorbed by a second substance different from the first substance in the specimen;
    a second pair of spaced-apart receivers mounted to said housing, each said receiver of said second pair configured to measure radiation at the second wavelength and being mounted to said housing to receive radiation from within the chamber; and
    a second pair of concave mirrors disposed in the housing chamber, said second pair of mirrors being shaped and positioned in the chamber to split the radiation emitted by said source into two beams each beam of radiation being directed to a separate one of said receivers that form said second pair of said receivers and so that paths of travel of the radiation beams from said source to said receivers forming said second pair of receivers are of different lengths.

11. The analysis apparatus of claim 1, wherein said first pair of mirrors are formed out of a single piece of material.

12. The analysis apparatus of claim 1, wherein said housing is arranged and said mirrors forming said first pair of concave mirrors are positioned so that a first one of the radiation beams has a sensor-to-receiver path of travel that is at least four times greater than the sensor-to-receiver path of travel of the second one of the radiation beams.

13. An analysis apparatus, said apparatus including:
    a housing, said housing having interior surfaces that are shaped to define an enclosed chamber for receiving a specimen to be analyzed;
    a radiation source mounted to said housing, said radiation source configured to emit radiation at a first wavelength that is absorbed by a first substance in the specimen, said radiation source mounted to said housing to emit radiation into the chamber;
    a first pair of spaced-apart receivers mounted to said housing, each said first pair receiver configured to measure radiation at the first wavelength and being mounted to said housing to receive radiation from within the chamber; and a first pair of concave mirrors formed by interior surfaces of said housing, said mirrors being shaped and positioned in the chamber to split the radiation emitted by said source into two beams, a first one of the beams being directed to a first one of said receivers of said first pair of receivers and a second one of the beams being directed to a second one of said receivers of said first pair of receivers and so that paths of travel of the radiation beams from said source to said receivers are of different lengths, wherein said first pair of concave mirrors are formed out of a single piece of material that forms said housing.

14. The analysis apparatus of claim 13, wherein at least one of said mirrors is an aspheric concave mirror.

15. The analysis apparatus of claim 13, wherein at least one of said mirrors is an aspheric concave mirror that is a section of a spheroid.

16. The analysis apparatus of claim 13, wherein said radiation source is an electrically modulable plane radiator.

17. The analysis apparatus of claim 13, wherein said housing is formed out of plural parts that are secured together, each said part having at least one surface that functions as a chamber-defining interior surface of said housing.

18. The analysis apparatus of claim 13, wherein;
said housing is formed out of first and second parts that are secured together, the first and second housing parts each having at least one surface that functions as a chamber-defining interior surface of said housing;
said first pair of mirrors are formed on the first part of said housing; and
said radiation source and said first pair of receivers are mounted to the second part of said housing.

19. The analysis apparatus of claim 18, wherein at least the first part of said housing is formed from metal.

20. The analysis apparatus of claim 18, wherein at least the first part of said housing is formed from aluminum.

21. The analysis apparatus of claim 13, wherein:
said radiation source is further configured to emit radiation at a second wavelength different from the first wavelength, the second wavelength radiation being radiation that is absorbed by a second substance different from the first substance in the specimen;
a second pair of spaced-apart receivers is mounted to said housing, each said second pair receiver configured to measure radiation at the second wavelength and being mounted to said housing to receive radiation from within the chamber; and
a second pair of concave mirrors formed by the material from which said first pair of concave mirrors are formed, said second pair of mirrors being shaped and positioned in the chamber to split the radiation emitted by said source so that two separate beams of radiation are directed to each of said receivers that form said second pair of said receivers and so that paths of travel of the radiation beams from said source to said receivers forming said second pair Of receivers are of different lengths.

22. The analysis apparatus of claim 21, wherein:
said housing is formed out of first and second parts that are secured together, the first and second parts each having at least one surface that functions as a chamber-defining interior surface of said housing;
said pairs of mirrors are formed from the first part of said housing; and
said radiation source and said pairs of receivers are mounted to the second part of said housing.

23. The analysis apparatus of claim 13, wherein said housing is arranged and said mirrors forming said first pair of concave mirrors are positioned so that a first one of the radiation beams has a sensor-to-receiver path of travel that is at least four times greater that the sensor-to-receiver path of travel of the second one of the radiation beams.

* * * * *